United States Patent
Stankov

(10) Patent No.: US 6,447,818 B1
(45) Date of Patent: Sep. 10, 2002

(54) **COMPOSITIONS CONTAINING COMPOUNDS WITH ADRENERGIC ACTIVITY AND VEGETABLE EXTRACTS OF CRATAEGUS AND *GINGKO BILOBA* FOR THE TREATMENT OF OVERWEIGHT AND OBESITY**

(75) Inventor: Bojidar M. Stankov, Milan (IT)

(73) Assignee: Ambros Pharma S.R.L., Milan (IT)

( * ) Notice: Subject to any disclaimer, the term of this patent is extended or adjusted under 35 U.S.C. 154(b) by 0 days.

(21) Appl. No.: 09/686,342

(22) Filed: Oct. 10, 2000

(30) Foreign Application Priority Data

Oct. 20, 1999 (IT) .......................................... MI99A2201

(51) Int. Cl.[7] ........................ A61K 35/78; A61K 31/52; A01N 43/90
(52) U.S. Cl. ........................ 424/752; 424/765; 424/736; 424/725; 424/439; 514/263; 514/909
(58) Field of Search .................................. 424/752, 725, 424/736, 765, 439; 514/12, 263, 909; 564/361

(56) References Cited

U.S. PATENT DOCUMENTS 5,958,417 A * 9/1999 Hsu
6,224,873 B1 * 5/2001 Jones
6,277,396 B1 * 8/2001 Dente

FOREIGN PATENT DOCUMENTS

DE 901791 * 3/1999
WO WO 98/14200 * 4/1998

OTHER PUBLICATIONS

Calapai et al., Fitoterapia (Dec. 1999), 70(6): 586–592. Antiobesity and cardiovascular toxic effects of Citrus aurantium extracts in the rat: a preliminary report.*

* cited by examiner

Primary Examiner—Christopher R. Tate
Assistant Examiner—Michele C. Flood
(74) Attorney, Agent, or Firm—Bucknam and Archer

(57) ABSTRACT

Compositions containing compounds with adrenergic activity and an extract of Crataegus standardized in flavonoids, combined with an extract of *Gingko biloba* standardized in flavonglucosides in appropriate weight ratios are suitable for pharmaceutical administration or as food supplements for the treatment of weight loss and obesity in humans. The formulations are appropriate for the administration of the active ingredients in a form that increases patient compliance and the efficacy of the therapeutic or dietary intervention, but reduces the untoward effects of the compounds with adrenergic activity.

17 Claims, 8 Drawing Sheets

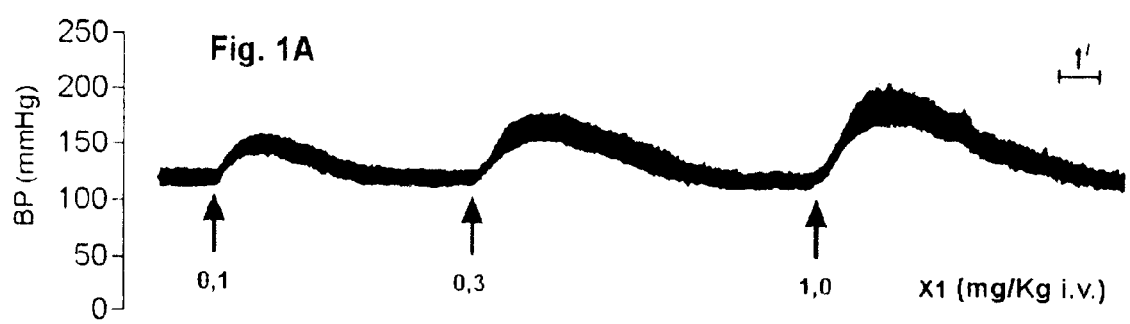
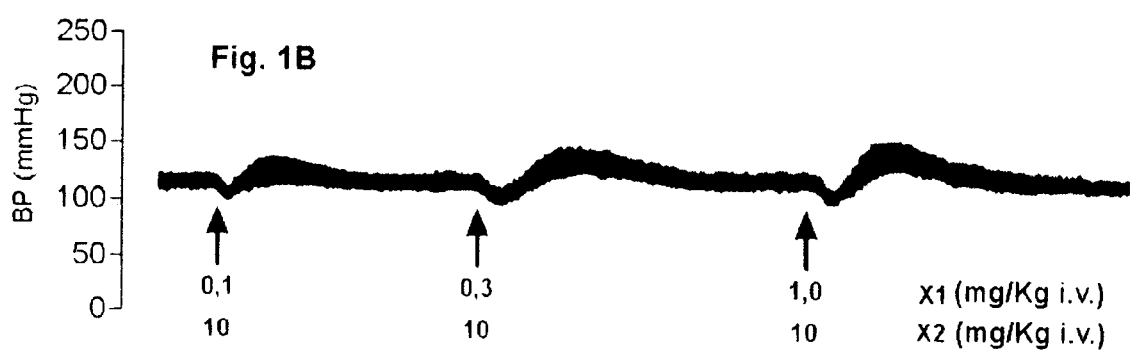

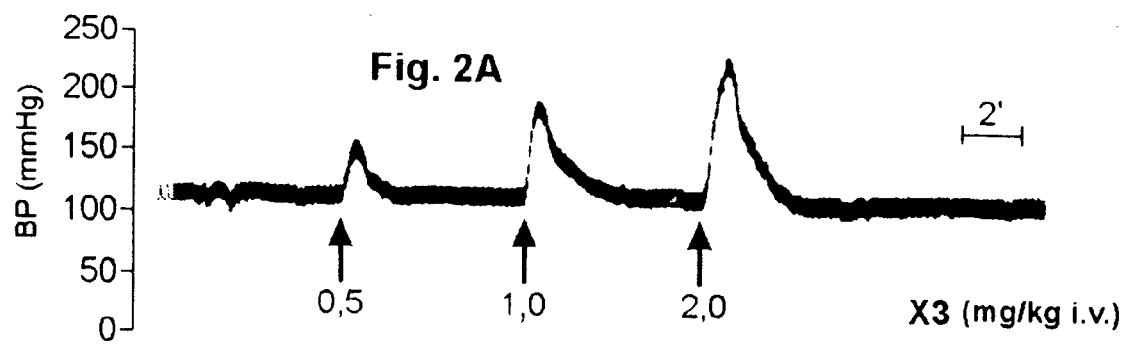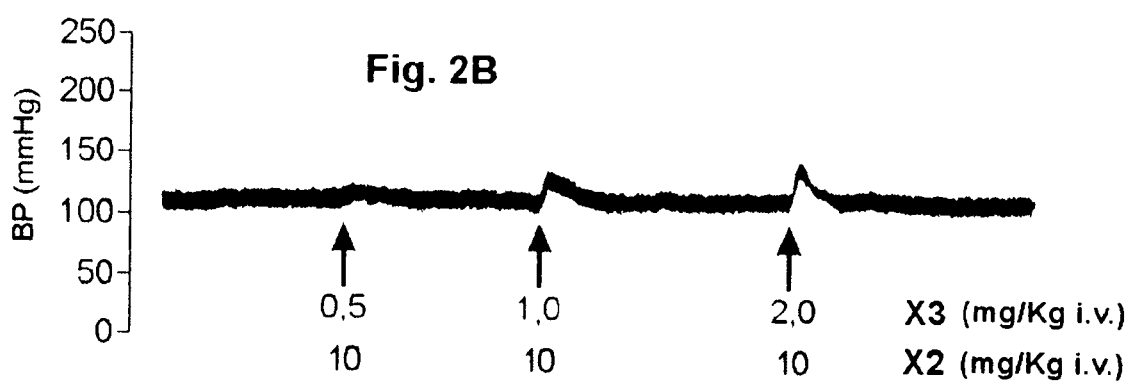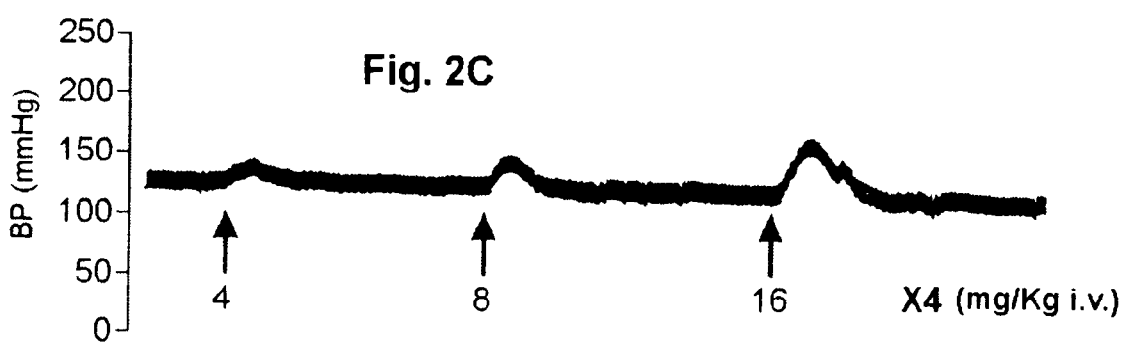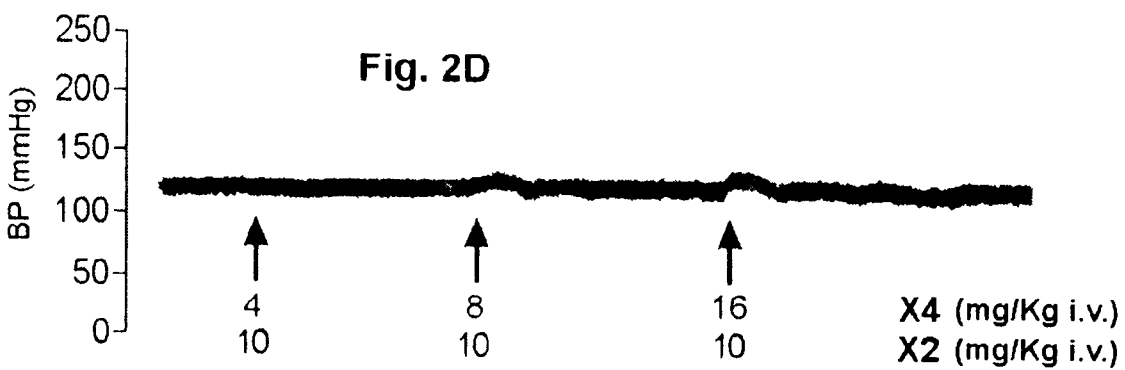

** P<0.01 for X2 vs X5 and X6; p<0.05 for X2 (10 mg/kg) vs X2 (2.5 mg/kg)

* p<0.05 for 5 mg/kg of X2 vs 0 and 2.5 mg/kg of X2
** p<0.01 for 10 mg/kg of X2 vs 0 and 2.5 mg/ kg of X2 and
p<0.05 for 10 mg/kg of X2 vs 5 mg/kg of X2

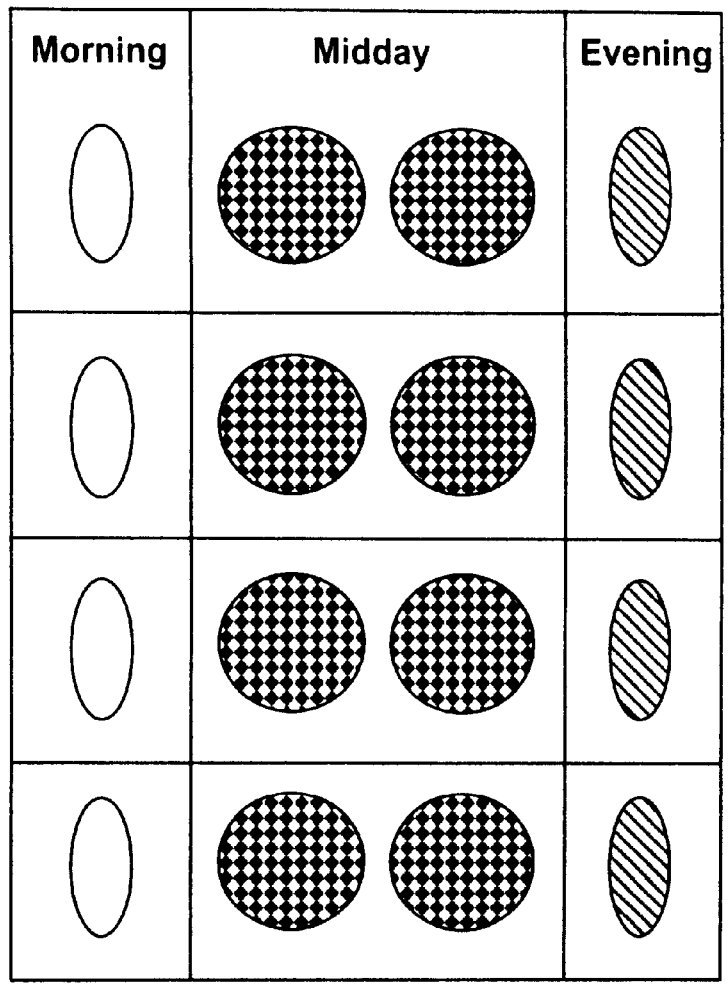
 1A
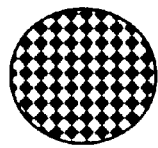 2A
 3
Fig. 5

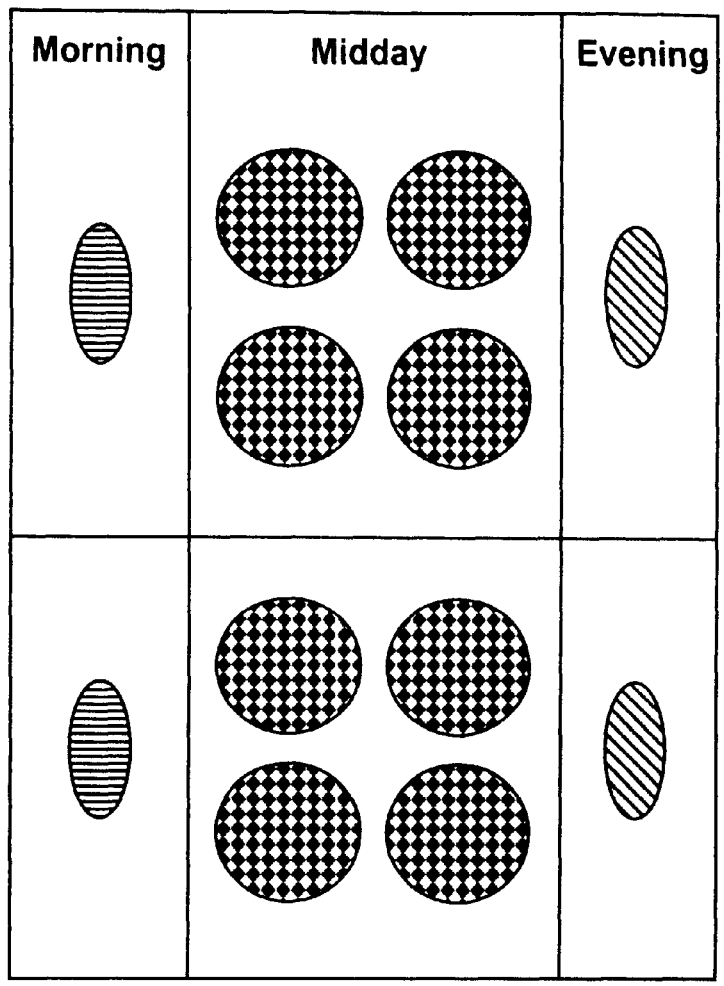
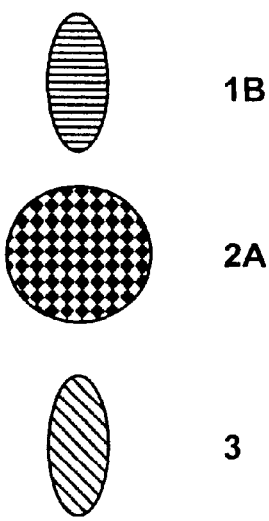
Fig. 6

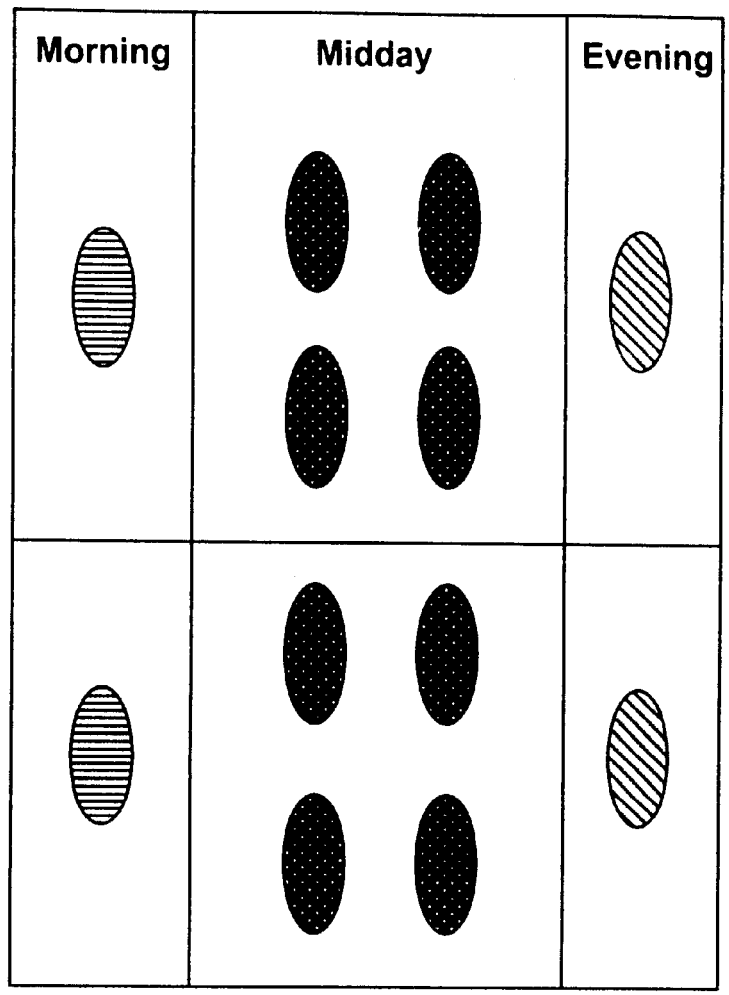
 1B
 2B
 3
Fig. 7

 1A
 2B
 3
Fig. 8

COMPOSITIONS CONTAINING COMPOUNDS WITH ADRENERGIC ACTIVITY AND VEGETABLE EXTRACTS OF CRATAEGUS AND *GINGKO BILOBA* FOR THE TREATMENT OF OVERWEIGHT AND OBESITY

FIELD OF THE INVENTION

This invention relates to compositions for the treatment of overweight and obesity.

BACKGROUND OF THE PRIOR ART

The management of body weight is a complex phenomenon that generally varies according to nutritive equilibrium. The amount of energy introduced with the intake of food and that used by the organism for the maintenance of vital functions (metabolism, respiration, thermoregulation, movement etc.) determines the energetic balance, which, if positive for long-term periods, inevitably leads to increased body weight and obesity.

In the last few years it has been clearly shown that weight-control diets are not efficient by themselves, while the use of drugs against obesity have significant side effects. The main problems associated with the control of body weight are the following:

a) The loss of weight, obtained by a low-calorie diet, gives rise, as a defense mechanism, to an exacerbated attraction for food, especially carbohydrates which are transformed into fat by the organism. Subsequently, the temporary weight loss is replaced by a fast and often uncontrolled weight increase.

b) The mobilization of fats from adipose deposits and their preferential use in metabolic processes occurs with difficulty and represents the hardest problem to face.

Modern research has shown that efficient weight management not only requires a reduction of the amount of energy introduced into the organism through the intake of fats and sugars (low-fat/low-calorie diets), but also the means of mobilizing the fat stored, that is, the use of substances with thermogenic action.

Thermogenesis is a metabolic process consisting of the production of heat by the organism, especially in the muscles and in the adipose tissues, using as energy source the available fat deposits. High thermogenesis allows body weight to decrease without significant variations in the quantity of food intake. The levels of thermogenesis vary from individual to individual, in a genetically predetermined way and for this reason body weight also varies from individual to individual regardless of the energetic limits set by the diet. The processes of thermogenesis are managed by the adrenergic system, through beta-3-adrenergic receptors.

Accordingly, the levels of thermogenesis can be altered with some adrenergic-like substances (adrenergic or sympathomimetic) such as, for instance, *ephedrine*, synephrine, amphetamine, phenylephrine etc. Adrenergic-like compounds are not very active alone in the activation of thermogenesis, and therefore, they are commonly used together with CNS stimulants, such as the methylxanthines: caffeine, theophylline and theobromine, which have a synergistic action with adrenergic substances.

The main problem associated with this approach consists of the fact that both adrenergic substances and methylxanthines produce significant side effects, particularly at cardiac-circulatory level, interacting with adrenergic receptors different from beta-3 receptors, and their administration is not recommended especially in hypertensive and borderline hypertension—patients, and may lead to serious adverse reactions. Incidentally, many overweight individuals that would benefit from the stimulation of thermogenesis are also hypertensive. The concomitant use of hypotensive drugs is to be avoided in all cases of borderline hypertension, because of the development of rebound phenomena. Of the natural extracts, Crataegus is known for its bland hypotensive activity. However, the disadvantages of the use of Crataegus are that: i) high dosages are required [approx. 400–800 mg/day]; ii) hypotension is often induced in normotensive patients Thus, natural alternatives are needed to avoid the side effects of the adrenergic substances used in the weight control management.

The other problem resides in the fact that the use of thermogenic substances alone is not sufficient for an effective long-term management of body weight. The simultaneous administration of other active ingredients is therefore required. For example, one of the substances used in weight control is food fiber. However this supplement must be administered separately since it interferes with the absorption of other nutrients if they are administered together.

SUMMARY OF THE INVENTION

The object of this invention is to provide compositions comprising at least one substance selected from the group consisting of *ephedrine*, pseudo-*ephedrine*, synephrine, tyramine, octopamine, methyltyramine, horderine, as a chemically pure substance or as a component of an extract of natural origin or any other compounds with adrenergic activity, or CNS stimulants, in combination with a Crataegus extract standardized, or not, in flavonoids associated with a *Gingko biloba* extract standardized, or not, in flavonglucosides.

This Crataegus extract contains flavonoids, and if combined with extract from *Gingko biloba* containing flavonglucosides, the resulting preparation exhibit unexpected synergistic activity in inhibiting the hypertensive and tachycariac effects of *ephedrine* and synephrine alone or together with other Central Nervous System stimulants.

This synergistic action is surprising since the same Crataegus extract, if not combined with the extract from *Gingko biloba*, does not by itself exert such activity at the dosages used and in order to show any anti-hypertensive activity, the dosages of must be 2 to 4 times higher. Moreover, the extracts of *Gingko biloba* do not exert hypotensive effects at any dosage.

If not otherwise specified, all the reagents used in the trials were obtained from Sigma, Chem. Co., St. Louis, Mo., USA. The extract of *Ephedra sinica*, standardized in 8% of *ephedrine*, the extract of Crataegus standardized in 2% flavonoids, the extract of *Ginkgo biloba* standardized in 24% flavonglucosides and the extract of *Citrus aurantium* standardized in 4% of synephrine was supplied by the company SOCHIM International, Milan. Exact quantities of the *Gingko biloba* extract were subsequently added to the extract from Crataegus, thereby obtaining in the course of the experiments one final vegetable composition standardized in 1.65% flavonoids and 6%-flavonglucosides. For convenience, in the description which follows this combination shall be called Oterin®. Therefore Oterin® is a new extract of Crataegus standardized in 1.65 flavonoids and enriched in 6% flavonglucosides from *Gingko biloba*.

BRIEF DESCRIPTION OF THE DRAWINGS

FIG. 1A shows example of the registration of the arterial pressure in the rat according to the quantity of X1 (*ephedrine*) administered.

FIG. 1B shows example of the registration of the arterial pressure in the rat according to the quantity of X1 (*ephedrine*) and of X2 (Oterin®=composition according to the invention) administered.

FIG. 2A shows example of the registration of the arterial pressure in the rat according to the quantity of X3 (synephrine) administered.

FIG. 2B shows example of the registration of the arterial pressure in the rat according to the quantity of X3 (synephrine) and of X2 (Oterin®) administered.

FIG. 2C shows example of the registration of the arterial pressure in the rat according to the quantity of X4 (*Citrus aurantium* extract) administered.

FIG. 2D shows example of the registration of the arterial pressure in the rat according to the quantity of X4 (*Citrus aurantium* extract) and of X2 (Oterin®) administered.

with X5 (physiological solution);
with X2 (Oterin®);
with X6 (normal Crataegus extract).

Figure 4:
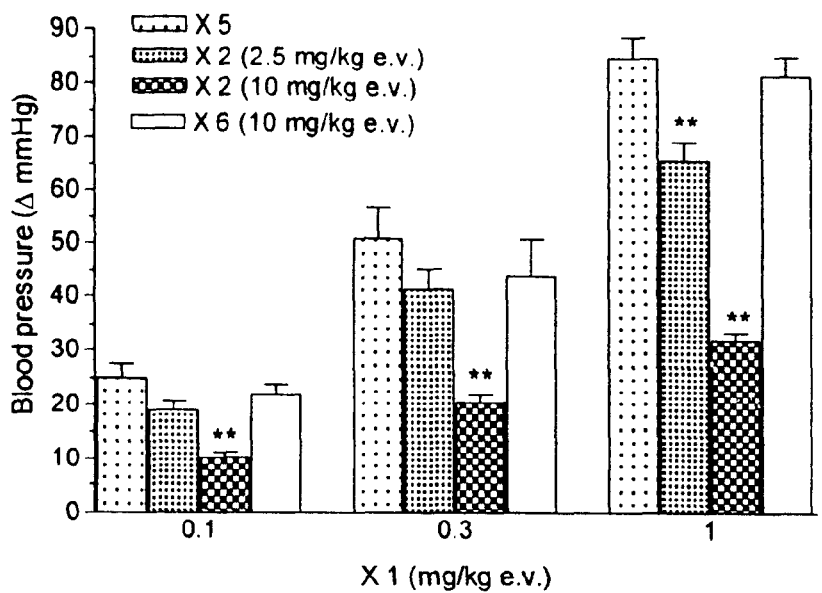
FIG. 4A shows mean increase in the arterial pressure in rats according to the quantity of X1 (Ephedrine) administered with the following combinations.
Figure 4:
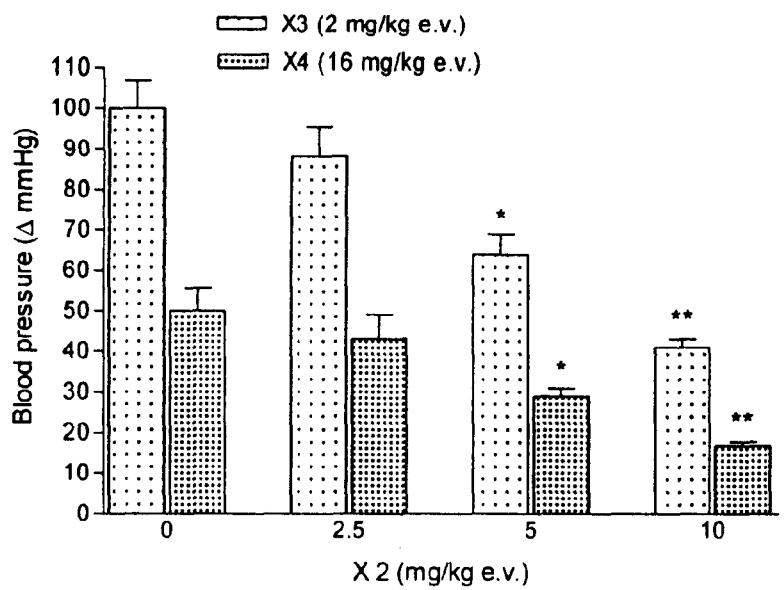

FIG. 4B shows the mean arterial pressure in rats after administration of X3 (synephrine) and of X4 (*Citrus aurantium* extract) according to the quantity of X2 (Oterin®) administered.

FIGS. 5, 6, 7 and 8 show examples of the Diversified Blister. The daily time of administration of the capsules or tablets is denoted on the top of the blister (morning, midday, evening). The lettering 1A and 1B, 2A and 2B and 3 correspond to various formulations given as non-limiting examples in the text, to be taken in the morning, midday and evening, respectively.

PHARMACOLOGICAL TRIALS

1. Effects of Crataegus Extract and Oterin® on Hypertension Induced with Ephedrine or with Extract of Ephedra Sinica Standardized in Ephedrine or Induced with Synephrine, or with Extract of Citrus Aurantium Standardized in Synephrine in the Rat Male Wistar rats (Charles River, Calco-CO) weighing 180–200 grams were used. The animals were anesthetized with ethylurethane (1.2–1.5 g/kg i.p.) and prepared for the recording of systemic arterial pressure (via the carotid artery) and cardiac frequency. Individual examples of the registration (copies of the original tracings) and the summary of the mean data (±SEM) are given in FIGS. 1–4.

Figure 3A:
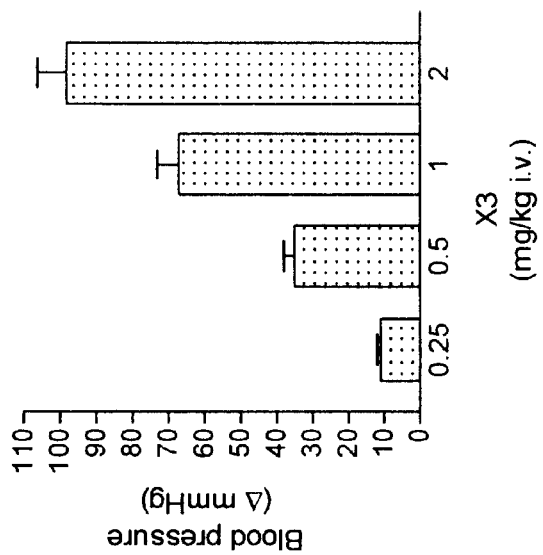
FIG. 3A shows mean increase in the cardiac frequency (Δ beats/min.) in rats according to the quantity of X3 (synephrine) administered. $p<0.05$ for every dose increment.
Figure 3C:
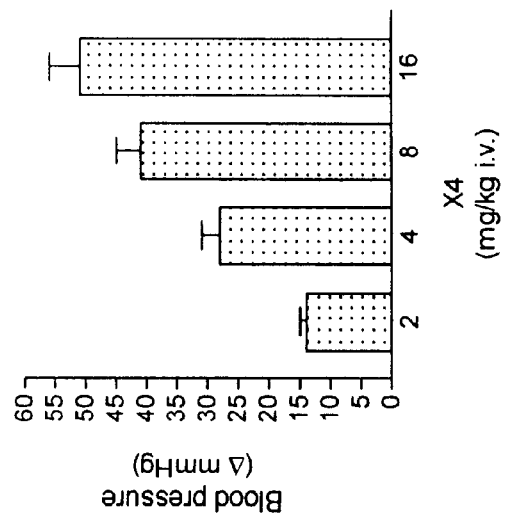
FIG. 3C shows mean increase in the arterial pressure in rats according to the quantity of X3 (synephrine) administered. $p<0.05$ for every dose increment.
Figure 3B:
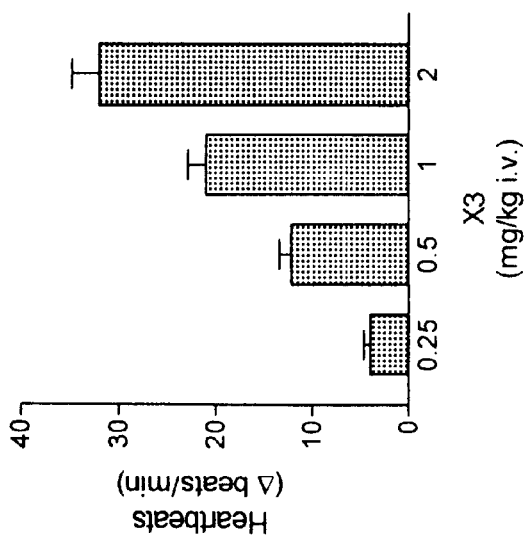
FIG. 3B shows mean increase in cardiac frequency (Δ beats/min) in rats according to the quantity of X4 (*Citrus aurantium* extract) administered. $p<0.05$ for every dose increment.
Figure 3D:
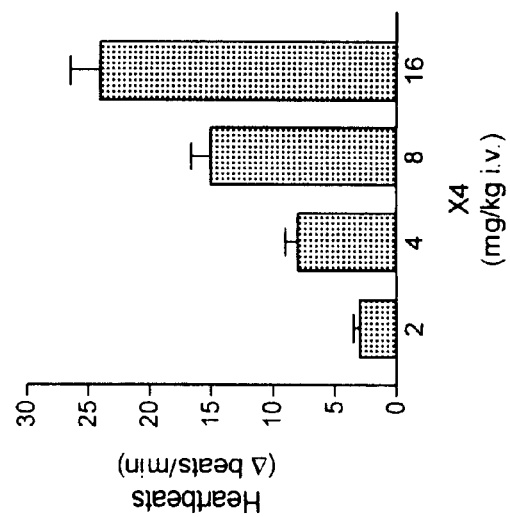
FIG. 3D shows mean increase in the arterial pressure in rats according to the quantity of X4 (*Citrus aurantium* extract) administered. $p<0.05$ for every dose increment.

The data clearly show that the administration of *ephedrine*, either pure or as an extract of *Ephedra sinica* standardized in *ephedrine*, exerts significant dose-dependent effects (between 0.1 and 1 mg/kg i.v.) on the arterial pressure (FIG. 1A). The dosages of synephrine leading to hypertensive activity were slightly higher (0.5–2 mg/kg i.v.) (FIGS. 2A, 3C). The dosages (between 1.25 and 12.5 mg/kg i.v. for the extract of *Ephedra sinica* standardized in 8% *ephedrine*; between 4 and 16 mg/kg i.v. for the extract of *Citrus aurantium*, standardized in 4% synephrine) necessary for inducing hypertensive effects (FIGS. 2C, 3D) reflected the content of *ephedrine* and synephrine in the respective extracts. Tachycardia was induced in the same dose-dependent manner (FIGS. 3A, 3B).

These data were considered very important since they clearly showed that both compounds (*ephedrine* and synephrine), either chemically pure or in the form of phytocomplex in vegetable extracts, likewise possess hypertensive activity in dosages corresponding to the contents of the active ingredients in the respective extract and the extracts induce hypertension and tachycardia.

Unexpectedly, the studies with Oterin® (FIGS. 1B, 2B, 2D, 4A and 4B) showed the appearance of a strong synergistic, non-additive effect of the two extracts present in Oterin®, since the effect of Oterin® was much higher than the sum of the individual effects obtained with the two extracts. The $ED_{50}$ (dose necessary to obtain 50% of the maximum anti-hypertensive effect) of Oterin® was approx. 8 mg/kg against an $ED_{50}$ of approx. 20 mg/kg of the Crataegus extract. Neither the Crataegus extract, nor the *Ginkgo biloba* extract alone had any anti-hypertensive effect at the dosages used for the preparation of Oterin®. Most importantly, Oterin® had no effect on the blood pressure and the heart frequency of the normotensive rat.

2. Effects of Oterin® on Induced Hypertension with the Extract of Efedra Sinica Standardized in Ephedrine or Extract of Citrus Aurantium Standardized in Synephrine, Independently Administered in Man, in the Presence of Caffeine The Study was carried out in blind, crossover design against placebo on volunteers with borderline hypertension (mean values: systolic pressure 152 mm; diastolic pressure 91.5 mm) of 49.1±3.13 years of age. The following formulations were administered: T1) Extract of *Ephedra sinica* with Guarana extract, each dosage containing: 20 mg of *ephedrine* and 100 mg of caffeine; T3) Extract of *Ephedra sinica* and Guarana extract each dosage containing: 20 mg of *ephedrine* and 100 mg of caffeine, together with 200 mg of Oterin®; T5) Extract of *Citrus aurantium* with Guarana extract each dosage containing: 24 mg of synephrine and 100 mg of caffeine; T7) Extract of *Citrus aurantium* and extract of Guarana each dosage containing: 24 mg of synephrine and 100 mg of caffeine, together with 200 mg of Oterin®. The treatments T2, T4 and T6 were placebo. A T8 treatment consisted of administering 200 mg of Oterin®.

Each treatment was carried out for three days followed by placebo for three days before the patient was admitted to the next treatment. The results (a summary is reported in Table I) clearly confirmed the laboratory data. In particular, the effects of the extract of *Ephedra sinica* and of *Citrus aurantium* used at the dosage of 20 and 24 mg/administration of *ephedrine* or synephrine, together with 100 mg of caffeine induced episodes of high pressure (higher than 160/100 in certain cases) in patients affected by borderline hypertension which made them purely hypertensive (all the patients had significantly higher blood pressure than before treatment, or with placebo, with an increase of 6–8 mm Hg from baseline). The heart frequency was similarly affected whereas the respiratory frequency did not significantly change. The dosages of *ephedrine*, synephrine and caffeine selected for the study were based on known data for the amounts required to stimulate thermogenesis and to induce body weight loss. These dosages has obviously led to an interaction of these substances with alfa- and as well beta adrenergic receptors, different from beta-3 receptors, inducing significant cardiocirculatory effects (increase in blood pressure and heart rate). The dosages of Oterin® were decided on the basis of the laboratory studies. Oterin® completely prevented the cardiovascular effects induced by the treatment, but did not influence the blood pressure in absence of adrenergic stimulation. In a separate trial Oterin® used in the same dosage (200 mg) was without effect on the vital parameters (blood, heart rate, respiratory rate) in normotensive healthy volunteers.

TABLE I

| Treatment | T1 | T3 | T5 | T7 |
|---|---|---|---|---|
| Systolic pressure (mm) | 159* | 149 | 160* | 150 |
| Diastolic pressure (mm) | 95.6* | 90.6 | 95* | 90.3 |
| Heartbeats/min | 95* | 83 | 89* | 82 |
| Breaths/min | 21 | 18.6 | 19 | 18.4 |

*$p < 0.05$ versus data obtained in the groups: T3, T7 (adrenegric stimulation plus Oterin ®, see text for details), T2, T4, T6 (placebo), T8 (placebo plus Oterin ®) and T0 (baseline)

The compositions according to the present invention can be administered to patients in the form of pharmaceutical formulations used for oral administration. The dosage generally used varies between approx. 150 and 300 mg of Oterin® daily for each patient. This is preferably administered with the extracts containing one of the following ingredients: *ephedrine*, pseudo-*ephedrine*, synephrine tyramine octopamine methyl-tyramine horderine in the form of chemically pure substances or as natural extracts or any other compound having an adrenergic activity and exerting thermogenic and lipolytic effects. Clearly, the effects found with Oterin® can also be obtained using compositions prepared by mixing given amounts of various other substances having the same characteristics, i.e.: flavonoids on one hand and flavonglucosides obtained from another natural extract containing those active ingredients.

The pharmaceutical compositions containing Oterin® are characterized by the fact that the weight ratio of the two components (Crataegus extract standardized in flavonoids and extract of *Gingko biloba* standardized in flavonglucosides) lies between approx. 1:1 and 10:1 and preferably between approx. 2:1 and approx. 6:1 and is more preferably 4:1 and they are able to counteact the hypertensive and cardiocirculatory effects of compounds having an adreno-agonistic activity. Preferred compositions to contrast obesity and overweight are those containing for each part in weight of *ephedrine* or of synephrine the following parts in weight:

methylxanthines (caffeine, theophylline or theobromine) :2.5–20;

Crataegus extract:1.8–15;

extract of *Gingko biloba* : 0.5–4;

The above compositions can also be used when they do not contain methylxanthines.

The above compounds may be employed for pharmaceutical use or can be added to other pharmacologically active or inactive ingredients so as to obtain forms of pharmaceutical dosage. The use of the compounds as drugs in the various forms of pathologies requires dosages corresponding to those given above.

A proper therapeutic approach to the treatment of overweight and obesity must satisfy the following criteria:

1) Limit the organic transformation of sugars into fat.
2) Increase the mobilization of fats from body deposits stimulating thermogenesis.
3) Stimulate the elimination of fats.
4) Naturally control the sensation of hunger.
5) Introduce sufficient quantities of food fiber.
6) Elude the cardiocirculatory effects of the substances inducing thermogenesis.

As explained above, the second problem in the treatment of overweight and obesity resides in the fact that the use of thermogenic substances is not sufficient for an effective long-term control of body weight. The simultaneous administration of other active ingredients is therefore required. One of the substances used for fighting overweight is food fiber. However, this essential supplement must be administered separately as it may interfere with the absorption of other nutrients if they administered together. At present, the complete therapeutic approach described above is feasible only by using and combining various products (usually two-three or more) with a consequent financial commitment but, most important of all, with significant problems of patient's compliance due to the number of products to be taken with different dosages: difficult to remember and follow. Moreover certain substances (e.g. Vitamin C) must be administered during the day, others (e.g. tryptophan) in the evening and yet others before meals (e.g. glucomannan or other fibers). These problems result in the uncertainty of the effectiveness of the treatment and often in its failure. The research of the applicant has led to the development of a new pharmaceutical form which is defined here as "Diversified Blister".

The diversified blister, unlike the normal blister, may include:

1. Any type of tablets together with any type of capsules
2. Capsules and tablets of various dimensions, as required
3. Variable number of capsules or tablets for each part of the blister. Moreover the diversified blister may bear indications regarding the timing of the administration (e.g. morning, midday, evening) of the different tablets or capsules with different size, if needed, and which may be diversified as well per form and color. Non-limiting examples are shown in FIGS. 5–8. In these Figures, the lettering 1A and 1B, 2A and 2B, and 3 correspond to various formulations given as non-limiting examples in the text, to be taken in the morning, midday and evening, respectively.

As shown in the Figures, the number of capsules or tablets may vary according to the type of treatment prescribed. Moreover the form of the capsules or tablets may also differ, for instance they may be ellipsoidal or discoid; the color and the size may vary as well. The diversified blister therefore resolves all the problems associated with the compatibility of the ingredients and the patient's compliance in the course of treatment for overweight and obesity.

Some formulations related to the compositions according to the invention, with information on dosage and administration, are given as non-limiting examples.

Formulation 1A (morning)
Swallowable tablets of 900 mg each

| Compound | Quantity (mg/tablet) |
| --- | --- |
| Citrus aurantium (s.e. 4% synephrine) | 250 |
| Guarana (s.e. 20% caffeine) | 250 |
| Oterin ® | 200 |
| Excipients | 200 |
| Dosage: One-Two tablets (morning) | Total: 900 mg/tablet | s.e., standardized extract

Formulation 1B (morning)
Swallowable tablets of 1250 mg each

| Compound | Quantity (mg/tablet) |
| --- | --- |
| L-Carnitine | 100 |
| Vitamin C | 60 |
| Citrus aurantium (s.e. 4% synephrine) | 300 |
| Cola (s.e. 50% caffeine) | 200 |
| Oterin ® | 200 |
| Excipients | 390 |
| Dosage: 1 tablet (morning) | Total: 1250 mg/tablet | s.e., standardized extract

Formulation 2A (midday)
Chewable tablets of 2850 mg

| Compound | Quantity (mg/tablet) |
| --- | --- |
| Apple fiber | 2000 |
| Apple flour | 408 |
| Hydroxycitric acid | 400 |
| Chromium polynicotinate (10% Cr) | 2 |
| Excipients | 40 |
| Dosage: Two-four chewable tablets at midday, before meal | Total: 2850 mg/tablet |

Formulation 2B (midday)
Swallowable capsules of 750 mg

| Compound | Quantity (mg/capsule) |
| --- | --- |
| Glucomannan | 750 |
| Chromium-polynicotinate (10%) | 0.5 |
| Dosage: Two-four capsules at midday, before meal | Total: 750.5 mg/capsule |

Formulation 3 (evening)
Swallowable capsules of 500 mg

| Compound | Quantity (mg/capsule) |
| --- | --- |
| L-Arginine | 300 |
| L-Methionine | 100 |

-continued

Formulation 3 (evening)
Swallowable capsules of 500 mg

| Compound | Quantity (mg/capsule) |
| --- | --- |
| L-Tryptophan | 75 |
| Vitamin $B_3$ | 9 |
| Excipients | 16 |
| Dosage: 1 capsule in the evening at bedtime | Total: 500 mg/capsule |

As described in the text. and shown in non-limiting manner in the examples of the formulations and the accompanying FIGS. (5–8), this invention comprises all the components required for food supplementation or pharmacological treatment of overweight and obesity in a single DIVERSIFIED BLISTER and therefore possesses the following properties:

1. Anorectic effect
2. Thermogenic and lypolytic effect for the elimination of fats
3. Metabolic effect: inhibition of new fat formation
4. Inhibiting effects on the centers of hunger in the central nervous system
5. Inhibiting effects on digestion and on the absorption of sugars and fats
6. Elimination of side effects of the thermogenic substances The data of this invention makes it possible to conclude that the Diversified Blister may be used, within the scope of the present invention, not only for substances employed in the treatment of overweight and obesity, but in all cases in which the daily administration of different components is required in individuals with various physical-pathological conditions.

It is also clear that the components with special indications for time of administration may be combined, within the scope of the present invention, thereby using other types of packaging different from the blister itself, such as for instance, jars containing tablets or capsules, sachets, or any other type of packaging commonly used in pharmaceutical practice.

The data of this invention indicate also that any form of active ingredient (for instance, other adrenergic compounds, their salts, mixed salts, complexes etc. in any bioavailable form, any extract of Crataegus and Gingko utilized in a similar way to that described in the present invention, or extracts of other plants containing similar active ingredients, may be used within the scope and the object of the present invention.

The formulations and the forms of dosages using the compositions of this invention may be prepared according to the customary methods employed in pharmaceutical practice, using, as well as active ingredients, support materials, excipients, diluting agents, emulsifying agents, water or oil vehicles, etc. acceptable to pharmaceutical practice.

For instance, solid formulations to be taken orally may contain, as well as the active composition, excipients such as mannitol, lactose, dextrose, sucrose, fructose, cellulose, corn or potato starch; lubricants such as silica, talc, magnesium oxide, stearate and/or polyethylenglycols; binding agents such as Arabic gum, methylcellulose, carboxymethylcellulose or polyvinylpyrrolidone; deagregating agents such as starch and alginates; effervescent mixtures; dyes; sweeteners; aromatizing agents; moisturizing agents such as polysorbates and laurylsulfate, various types of soluble or insoluble, digestible or not-digestible fiber. Moreover formulations may be supplied in any classical pharmaceutical forms such as hard capsules, soft capsules, tablets, sachets, solutions, chewable forms, etc. Suspensions and emulsions may contain vehicles of active ingredients such as natural gum, sodium alginate, carboxymethylcellulose or polyvinyl alcohol, various types of fiber. The compositions of this invention may also be used with vehicles suitable for transmucosal, topic or transdermic administration.

The compositions associated with this invention may also be used for the preparation of foods, or herbal products, or food supplements, that is, preparations which in a complex dietary management may integrate the diet in individuals having intra- and extracellular deficiencies in the above components and therefore with altered metabolic processes.

What is claimed is:

1. A weightloss composition for managing body weight comprising effective therapeutic amounts of at least one or more substances selected from the group consisting of *ephedrine*, pseudo-*ephedrine*, synephrine tyramine, octopamine, methyl tyramine, and horderine in combination with a Crataegus extract containing standardized amounts of flavonoids and an extract of *Gingko biloba* containing standardized amounts of flavonglucosides, wherein the weight ratio between the Crataegus extract and the extract of *Gingko biloba* ranges between approximately 1:1 and 10:1.

2. A composition according to claim 1, wherein the weight ratio ranges between approximately 2:1 and 6:1.

3. A composition according to claim 2, wherein the weight ratio is 4:1.

4. A composition according to claim 1, containing *ephedrine* or an extract of *Ephedra sinica* containing standardized amounts of *ephedrine*, and other components wherein for every part in weight of *ephedrine* the parts in weight of said other components are included in the following ranges: caffeine 2.5–20; Crataegus extract 1.8–15; extract of *Gingko biloba* 0.5–4.

5. A composition according to claim 1, containing synephrine or an extract of *Citrus aurantium* containing standardized amounts of synephrine, and other components wherein for every part in weight of synephrine the parts in weight of said other components are included in the following ranges: caffeine 2.5–20; Crataegus extract 1.8–15; extract of *Gingko biloba* 0.5–4.

6. A composition according to claim 1, containing other components wherein for every part in weight of *ephedrine* the parts in weight of said other components are included in the following ranges: theophilline or theobromine 2.5–20; Crataegus extract 1.8–15; *Gingko biloba* extract 0.5–4.

7. A composition according to claim 1, containing other components wherein for every part in weight of synephrine the parts in weight of said other components are included in the following ranges: theophilline or theobromine 2.5–20; Crataegus extract; 1.8–15; *Gingko biloba* extract 0.5–4.

8. A composition according to claim 1, in which for every part in weight of *ephedrine* or synephrine the parts in weight of the other components are included in the following ranges: Crataegus extract 1.8–15; *Gingko biloba* extract 0.5–4.

9. A composition according to claim 1, for the preparation of formulations for the treatment of obesity.

10. A composition according to the claim 1, in a form suitable for oral administration.

11. A process for the preparation of a composition according to claim 1, which comprises mixing therapeutically effective amounts of a Crataegus extract containing standardized amounts of flavonoids and an extract of *Gingko biloba* containing standardized amounts of flavonglucosides with *ephedrine* or with synephrine to obtain a composition of pharmaceutical dosage.

12. The process according to claim 11, wherein caffeine or other methylxanthines and other pharmacologically active or inactive ingredients are used to obtain forms of pharmaceutical dosage.

13. The composition as defined in claim 5 for the preparation of a pharmaceutical product, a food supplement, a food, an herbal or cosmetic product mixed with acceptable ingredients for food, cosmetic or pharmaceutical use.

14. A composition according to claim 1, which is prepared in tablets or capsules packaged in a diversified blister as in size, form and color, and bearing information related to times of the daily administration.

15. A composition according to claim 14, wherein the said blister contains capsules or tablets that differ in size or form which may be ellipsoidal or discoid.

16. A composition according to claim 14, wherein in the said blister the capsules or tablets are identified for intake in the morning, midday and evening by form, color or lettering.

17. A composition according to claim 14, wherein in the said blister the number of capsules or tablets varies according to the treatment prescribed.

* * * * *